(12) United States Patent
Gelmont et al.

(10) Patent No.: US 6,380,440 B1
(45) Date of Patent: Apr. 30, 2002

(54) PROCESSES FOR THE PREPARATION OF 3-BROMOANISOLE AND 3-BROMONITROBENZENE

(75) Inventors: Mark Gelmont, Nesher; Joseph Zilberman, Haifa, both of (IL)

(73) Assignee: Bromine Compounds Ltd. (IL)

( * ) Notice: Subject to any disclaimer, the term of this patent is extended or adjusted under 35 U.S.C. 154(b) by 0 days.

(21) Appl. No.: 09/680,961

(22) Filed: Oct. 5, 2000

Related U.S. Application Data

(63) Continuation of application No. PCT/IL99/00161, filed on Mar. 22, 1999.

(30) Foreign Application Priority Data

Apr. 7, 1998 (IL) .................................................. 123990

(51) Int. Cl.⁷ .............................................. C07C 41/00
(52) U.S. Cl. ...................................... 568/656; 568/937
(58) Field of Search .................................. 568/937, 656

(56) References Cited

U.S. PATENT DOCUMENTS 2,607,802 A * 8/1952 Britton
4,418,228 A 11/1983 Harrison et al. ............ 568/937

FOREIGN PATENT DOCUMENTS

EP 0 408 759 A1 1/1991

OTHER PUBLICATIONS

Carpenter, M.S., et al. "Nitro musks. I. Isomers, homologs, and analogs of musk ambrette" Journal of Organic Chemistry, vol. 16, 1951, pp. 586–617, Easton US, XP002108860.

Effenberger, F., et al. "Nucleophile Substitution von Nitrit in Nitrobenzolen, Nitrobiphenylen und Nitronaphthalinen" Berichte Der Deutschen Chemischen Gesellschaft, vol. 124, 1991, pp. 163–173, Weinheim DE, XP002108861.

Khan, S.A., et al. "Monobromination of deactivated active rings using bromine, mercuric oxide, and strong acid" Journal of Organic Chemistry, vol. 53, 1988, pp. 1799–1800, Easton US, XP002108862.

Harrison, J.J., et al. "Bromination of deactivated aromatics using potassium bromate", Journal of Organic Chemistry, vol. 46, No. 10, 1981, pp. 2169–2171, Easton US, XP002108863.

Hewett, C.L. "The Synthesis of Compounds related to the Sterols, Bile Acids, and Oestrus–producing Hormones. Part VIII." J. Chem. Soc., vol. 50, 1936, pp. 50–52.

Natelson, S. and Gottfried, S.P. "Synthesis of Derivatives of Symmetrical Diphenylethane Related to Materials Occurring Naturally. II. 3,4–Dihydro–5–methyl–3'–methoxydibenzyl, a Compound Related to Oestrone in Structure" J. Amer. Chem. Soc., vol. 61, 1939, pp. 1001–1002.

Berti, G. et al. "Basicita secondaria di alcuni carbinoli derivati del dibenzo–cicloeptatriene e del dibenzo–cicloeptadiene." Ann. Chim., vol. 49, 1959, pp. 1237–1252.

Johnson, J.R. and Gauerke, C.G. "m–Bromonitrobenzene" "Organic Synthesis", Coll., vol. 1, 1956, pp. 123–124.

Tronov, B.V., et al. "Halogenation of aromatic hydrocarbons and their derivatives in the presence of a nitration mixture." Chem. Abstr. 55:8347i.

Tronov, B.V., et al. "Effect of various catalysts on the direction and rate of bromination of aromatic compounds." Chem. Abstr. 49:13133d.

Derbyshire, D.H. and Waters, W.A. "The Significance of the Bromine Cation in Aromatic Substitution. Part II. Preparative Applicability." J. Chem. Soc., 1950, pp. 573–577.

\* cited by examiner

*Primary Examiner*—Michael L. Shippen
(74) *Attorney, Agent, or Firm*—Lerner, David, Littenberg, Krumholz & Mentlik, LLP

(57) ABSTRACT

Process for the preparation of 3-bromoanisole comprising methoxydenitrating 3-bromonitrobenzene in the presence of a phase-transfer catalyst (PTC), and the preparation of 3-bromonirtobenzene by the bromination of nitrobenzene with bromine in oleum. The methoxydenitration reagent in an alkali metal methoxide, which is selected from sodium methoxide and potassium methoxide. The amount of methoxide used is 1–1.5 mol per mol of 3-bromonitrobenzene. The alkali methoxide can be a pre-prepared solid or it can be prepared in situ, by the reaction of the corresponding alkali hydroxide and methanol. In the case when pre-prepared solid methoxide is used, the effective amount of alkali hydroxide is between 1.2–1.7 mol per mol of 3-bromonitrobenzebe. The reaction temperatures are between about 40 to 80° C., with preference to reaction temperatures of 50 to 55° C. In the case in which methoxide is prepared in situ, the effective amount of alkali hydroxide is between 2.2-2.4 mol per mol of 3-bromonitrobenzene. The reaction temperatures are between about 50 to 80° C. with preference to reaction temperatures of 55 to 65° C.

35 Claims, No Drawings

PROCESSES FOR THE PREPARATION OF 3-BROMOANISOLE AND 3-BROMONITROBENZENE

This application is a continuation of international application number PCT/99/00161 filed Mar. 22, 1999.

FIELD OF THE INVENTION

This invention relates to a process for the preparation of 3-bromoanisole by the methoxydenitration of 3-bromonitrobenzene in the presence of a phase transfer catalyst.

BACKGROUND OF THE INVENTION

3-Bromoanisole (hereinafter indicated also as MBA) is an intermediate in the pharmaceutical field. In particular, it is used for producing the analgesic drug Tramadol.

Among the few known methods for preparing MBA, the most frequently encountered one is that based on the methylation of meta-bromophenol. See, for example, Hewett, J. Chem. Soc. 50 (1936) and Natelson, Gottfried, J. Amer. Chem. Soc. 61, 1001 (1939). Meta-bromophenol in turn is prepared by diazotization starting from meta-bromoaniline or meta-aminophenol. Berti et al., Ann. Chim., 49, 1237, 1248 (1959) reports a method for preparing MBA from meta-anisidine, via a diazotization reaction.

The principal disadvantage of these known processes for the industrial preparation of MBA is that they are based on expensive and insufficiently accessible starting materials. An additional disadvantage consists in the large amounts of aqueous wastes produced in the diazotization process. It is a purpose of this invention to provide a new and convenient route for the preparation of MBA, which starts from 3-bromonitrobenzene, and provides the final MBA in high yield and with good purity.

3-Bromonitrobenzene (hereinafter also designated as BNB) can be prepared by several known routes. Johnson and Gauerke, "Organic Synthesis", Coll. Vol. 1, 123–124 (1956) examined bromination of nitrobenzene with bromine in the presence of iron powder, at a temperature of 135–145° C. The yield of BNB was 60–75%. Several other catalysts were tested by Tronov et al. (Chem. Abstr. 55:8347i and 49:13133d), who obtained 33% BNB by using bromine, sulphuric, nitric and acetic acid at a temperature of 83° C. over a period of 4–5 hours, or with bromine and catalysts such as aluminum, sulphur and tellurium. Derbyshire and Waters, J. Chem. Soc., 573–577 (1950) reported that nitrobenzene may be brominated by reaction with hypobromous acid. Bromination of nitrobenzene with potassium bromate was reported in U.S. Pat. No. 4,418,228 and J. Org. Chem., 46, 2169–2171. They claimed that equimolar amounts of bromate and nitrobenzene in 65% sulphuric acid afforded BNB, after 24 hours at 35° C., with a yield of 88%. The main deficiency of this method is the need for relatively expensive and technically difficult to use, alkali metal bromate.

Thus, another purpose of this invention is to provide a new and convenient route for the preparation of BNB, by the bromination of nitrobenzene with bromine in oleum to overcome the problems connected with the use of alkali metal bromate.

Other purposes and advantages of the invention will better appear as the description proceeds.

SUMMARY OF THE INVENTION

The invention provides a process for the preparation of 3-bromoanisole comprising methoxydenitrating 3-bromonitrobenzene in the presence of a phase-transfer catalyst (PTC), and the preparation of 3-bromonitrobenzene by the bromination of nitrobenzene with bromine in oleum.

In one aspect, the invention is directed to a process for the preparation of 3-bromoanisole comprising methoxydenitrating 3-bromonitrobenzene in the presence of a phase-transfer catalyst. According to a preferred embodiment of the invention, the methoxydenitration reagent is an alkali metal methoxide. Preferably, the alkali metal methoxide is selected from sodium methoxide and potassium methoxide.

According to a preferred embodiment of the invention, the amount of methoxide used is 1–1.5 mol per mol of 3-bromonitrobenzene. The alkali methoxide can be a pre-prepared solid or it can be prepared in situ, by the reaction of the corresponding alkali hydroxide and methanol. Typically, in the case when pre-prepared solid methoxide is used, the effective amount of alkali hydroxide is between 1.2–1.7 mol per mol of 3-bromonitrobenzene. Typical reaction temperatures are between about 40 to 80° C. Preferred reaction temperatures are between 50 to 55° C.

In the case in which methoxide is prepared in situ, the effective amount of alkali hydroxide is between 2.2–2.4 mol per mol of 3-bromonitrobenzene. Typical reaction temperatures are between about 50 to 80° C. Preferred reaction temperatures are between about 55 to 65° C.

The concentration of phase transfer catalyst can be easily selected by the skilled chemist for specific reaction conditions. Illustrative—but non-limitative concentrations of phase transfer catalyst are in the range of 20 to 30 wt % relative to the initial BNB. Examples of suitable phase transfer catalysts include tributylmethylammonium chloride, tetrabutylammonium chloride, tetrabutylammonium hydroxide, tetrabutylammonium hydrogen sulfate, or tetrabutylammonium bromide. Other suitable PTCs will be easily recognized by the skilled person.

In another aspect the invention relates to a process for the preparation of 3-bromonitrobenzene, comprising reacting nitrobenzene with bromine in oleum as the reaction medium. Optionally, the reaction can be carried out in the presence of iodine. Small amounts of iodine, e.g., amounts of up to 5% by weight relative to the substrate are usually sufficient. Preferred (but non-limitative) iodine contents are in the rang 0–5% weight % relative to the nitrobenzene, more preferably about 0.2–0.5 weight %. Iodine acts in this process as a catalyst and, therefore, low amounts of iodine are sufficient.

The oleum contains free $SO_3$. The content of free $SO_3$ in the oleum is typically about 1–65%. According to a preferred embodiment of the invention, however, the oleum contains about 15–30% free $SO_3$.

Typical reaction temperatures are between about 0–100°. According to a preferred embodiment of the invention the reaction temperature is between about 20–40° C.

The oleum/nitrobenzene weight ratio may vary, and is typically between about 1.5 and 10.

According to a preferred embodiment of the invention the $Br_2$/nitrobenzene molar ratio is in the range of 0.3 to 1, more preferably in the range of 0.4 to 0.5.

According to a preferred embodiment of the invention the bromination mixture is further processed by one of the following procedures:

Procedure A:
  a) diluting with water; and
  b) phase separation at a temperature above 50° C.

Procedure B:
  a) diluting with water; and
  b) cooling and filtering the crystallized 3-bromonitrobenzene.

Procedure C:
a) diluting with water;
b) extracting the 3-bromonitrobenzene with an organic solvent; and
c) phase separation. Various different solvents can be employed in the reaction of the invention, as will be easily understood by the skilled person. Illustrative suitable solvents include dichloroethane, dichloromethane, toluene, xylene or cyclohexane.

In still another aspect the invention encompasses a process for the preparation of 3-bromoanisole, comprising the steps of:
a) preparing 3-bromonitrobenzene by reacting nitrobenzene with bromine in oleum as the reaction medium.
b) preparing 3-bromanisole from said 3-bromonitrobenzene by methoxydenitrating 3-bromonitrobenzene in the presence of a phase-transfer catalyst (PTC).

All the above and other characteristics and advantages of the invention will be better understood through the following illustrative and non-limitative detailed description of preferred embodiments thereof.

DETAILED DESCRIPTION OF PREFERRED EMBODIMENTS

Preparation of 3-Bromonitrobenzene

BNB is prepared by a new process, comprising reacting nitrobenzene with bromine, in oleum, optionally in the presence of iodine.

According to a preferred embodiment of the invention, the oleun contains about 1–65% free $SO_3$. Preferably, but non-limitatively, the oleum contains about 15–30% free $SO_3$.

While a broad range of iodine contents is permissible, according to a preferred embodiment of the invention, iodine is present in an amount of about 0–5 wt % relative to nitrobenzene, preferably but not Imitatively 0.2–0.5 wt % relative to the nitrobenzene.

As will be apparent to a person skilled in the art, the process of the invention can proceed in a very broad range of temperatures. According to a preferred embodiment of the invention, however, the reaction temperature is kept between about 0–100° C., and more preferably, 20–40° C.

The oleum/nitrobenzene weight ratio can vary within a broad range. According to a preferred embodiment of the invention, however, the oleum/nitrobenzene weight ratio is between about 1.5 and 10.

The $Br_2$/nitrobenzene molar ratio is also variable within a broad range, typically in the range of 0.3–1.0. According to a preferred embodiment of the invention, the $Br_2$/nitrobenzene molar ratio is in the range of 0.4–0.5.

The working-up of the bromination mixture may be carried out by several methods:
a) Dilution with water followed by phase separation at a temperature above 50° C.
b) Dilution with water, cooling and filtering of the crystallized, crude BNB.
c) Dilution with water, followed by extraction of the crude BNB with an organic solvent (dichloroethane, dichloromethane, toluene, xylene, cyclohexane, etc.) and phase separation. A variation of this may be extraction without previous dilution. In this case, part of the used oleum may be returned to the next bromination, after make-up with oleum, 65% free $SO_3$ oleum.

The purification of the crude BNB may be carried out by distillation or by crystallization from methanol, ethanol, isopropanol, etc.

BNB was obtained with a yield of ~80%, based on reacted nitrobenzene, and a purity of 98–99% after distillation.

Preparation of 3-Bromoanisole

3-Bromoanisole is prepared by nucleophilic substitution of the nitrate group in BNB. The methoxydenitration of BNB is carried out by its reaction with alkali metal methoxide such as sodium methoxide or potassium methoxide, employing an effective amount of a phase transfer catalyst (PTC), in a medium of a water-immiscible nonpolar aprotic solvent, such as cyclohexane, hexane, heptane, octane, nonane, xylenes, and preferably, toluene.

An effective amount of PTC is employed in a range of from 20 to 30% w/w, based on the initial BNB. The PTC is selected from quaternary ammonium salts. Especially suitable phase transfer catalysts are tributylmethylammonium chloride, tetrabutylammonium chloride, tetrabutylammonium hydroxide, tetrabutylammonium hydrogen sulfate, and in particular, tetrabutylammonium bromide.

Two different methods of employing the alkali metal methoxide are suggested. The first method consists in using pre-prepared solid alkali metal methoxide. The reaction is carried out using sodium or potassium methoxide, with sodium methoxide being preferred, in the presence of an effective amount of potassium hydroxide. The amount of methoxide used is 1.1–1.2 mol, based on 1 mol BNB. An effective amount of potassium hydroxide is comprised of between 1.2–1.7 mol, and preferably 1.4–1.7 mol with respect to 1 mol BNB. Said reaction is carried out at a temperature of between 40 and 80° C., and preferably between 50 and 55° C.

The second method of carrying out the methoxydenitration employs potassium methoxide prepared in situ, in the course of the reaction, from methanol and potassium hydroxide. The amount of methanol used is 1.1–1.2 mol, based on 1 mol BNB. The amount of potassium hydroxide is comprised between 2–2.4 mol, and preferably between 2.2–2.4 mol, with respect to 1 mol BNB. Said reaction is carried out at a temperature of between 50 and 80° C., and preferably between 55 and 65° C.

The reaction may also be performed with sodium methoxide prepared in situ from methanol and sodium hydroxide. However, sodium methoxide so prepared is considerably less reactive than potassium methoxide.

In both methods, some water may optionally be added to the starting reaction mixture, in order to partially dissolve the solid potassium hydroxide, and thus to facilitate stirring of the heterogeneous mixture.

The reaction should be performed under aerobic conditions in order to suppress the radical processes leading to the formation of products of nitro reduction, mainly hydrodebromination to nitrobenzene and nitro reduction to 3,3'-dibromoazoxybenzene and 3,3'-dibromoazobenzene.

The crude MBA so obtained is purified by means of fractional distillation. The fractional distillation may be carried out in the presence of an alkali such as sodium hydroxide or potassium hydroxide, as will be described hereinafter.

The processes according to the invention provide 3-bromonitrobenzene and 3-bromoanisole in good yields and with high purity.

A number of illustrative and non-limitative embodiments of the invention will now be described, with reference to the examples below.

EXAMPLE 1

Preparation of BNB by the Brorination of Nitrobenzene in Oleum

Into a 1-liter flask equipped with a mechanical stirrer, a condenser, a thermometer and a dropping funnel, are introduced, at room temperature, 1.24 g iodine and 427 g $H_2SO_4$ (97%) and, with stirring and cooling, 316 g oleum (65% free $SO_3$). 246 g (2 mole) nitrobenzene is added dropwise over one hour at a temperature in the range of 10–12° C., then 128 g (0.8 mole) bromine is added dropwise over 2.5 hours at a temperature of 20° C. Stirring is continued for an additional 2.5 hours at 30° C. Samples are removed during the bromination to check the reaction conversion by GC analysis. After completion of the reaction, the reaction mixture is added carefully to 540 g water at 70–80° C. over 0.5 hr. 350 g crude BNB is obtained after phase separation at 60° C., and is distilled at 100–130° C. at a pressure of ~20 mm Hg, to give 230 g BNB with a purity of 98–99% (GC, area). About 75 g nitrobenzene distills as a first fraction, and is used in the next experiment. The yield is ~81%, based on reacted nitrobenzene.

The results of this specific example are detailed in the following table (Experiment 1).

Several similar experiments were carried out. The reaction conditions and the results of the experiments are presented in the table. The abbreviations used throughout this table are as follows:

| | |
|---|---|
| NB | Nitrobenzene |
| 4BNB | 4-Bromonitrobenzene |
| DBNB | Dibromonitrobenzene |
| o.n. | overnight. |

TABLE I

Bromination of nitrobenzene in oleum.

| Exp. No. | NB g/mole | Iodine % w/w NB | Oleum g/conc. | Bromine g/mole | Temp. ° C. | Time hr | NB %, GC | BNB %, GC | 4BNB %, GC | DBNB1/DBNB2/DBNB3 %, GC |
|---|---|---|---|---|---|---|---|---|---|---|
| 1 | 246/2.0 | 0.5 | 744/20 | 128/0.8 | 20–30 | 3 | 42.2 | 53.6 | 1.6 | 0.2/0.7/0.2 |
| | | | | | | 5 | 33.2 | 63.1 | 1.7 | 1.5/0.4/0.2 |
| 2 | 62/0.5 | 0.5 | 310/20 | 40/0.25 | 10 | 3 | 53.2 | 44.0 | 1.0 | 1.0/0.3/— |
| | | | | | | 5 | 39.5 | 56.3 | 1.2 | 2.1/0.7/0.2 |
| | | | | | | 6.5 | 32.7 | 61.9 | 1.3 | 2.7/0.9/0.4 |
| 3 | 124/1.0 | 0.5 | 620/20 | 72/0.45 | 20 | 3 | 29.8 | 62.5 | 1.4 | 3.4/1.3/0.3 |
| | | | | | | 4.5 | 24.1 | 66.8 | 1.6 | 4.5/1.8/0.4 |
| | | | | | | o.n. | 9.3 | 76.2 | 1.7 | 7.8/3.1/0.7 |
| 4 | 62/0.5 | 0.5 | 248/20 | 32/0.2 | 30 | 1 | 48.9 | 47.2 | 1.3 | 1.2/0.5/0.1 |
| | | | | | | 3 | 16.3 | 71.2 | 1.7 | 6.3/2.5/0.6 |
| | | | | | | 4 | 8.2 | 75.1 | 1.5 | 9.0/3.5/0.8 |
| 5 | 62/0.5 | 0.5 | 248/98 $H_2SO_4$ | 64/0.4 | 30–90 | 5 | 98.9 | 1.1 | — | — |
| 6 | 62/0.5 | 0.5 | 248/10 | 32/0.2 | 30 | 2 | 54.2 | 43.8 | 1.1 | 0.8/—/— |
| | | | | | | 5 | 48.5 | 48.4 | 1.2 | 1.2/0.4/— |
| | | | | | | 6 | 43.9 | 52.9 | 1.3 | 1.5/0.4/— |
| | | | | | | 8 | 42.8 | 54.3 | 1.4 | 1.5/0.4/— |
| 7 | 62/0.5 | 0.5 | 186/120 | 32/0.2 | 30 | 2 | 24.3 | 65.8 | 1.6 | 3.6/1.2/0.3 |
| | | | | | | 3 | 21.0 | 70.1 | 1.5 | 4.5/1.5/0.4 |
| | | | | | | 4 | 21.4 | 69.9 | 1.6 | 4.4/1.4/0.4 |
| 8 | 62/0.5 | 0.5 | 155/20 | 32/0.2 | 30 | 2 | 67.3 | 30.5 | 0.7 | 1.0/0.8/0.1 |
| | | | | | | 3 | 68.4 | 29.7 | 0.7 | 1.0/0.3/— |
| 9 | 62/0.5 | 0.2 | 186/20 | 32/0.2 | 30 | 2 | 35.1 | 60.2 | 1.5 | 2.4/0.8/— |
| | | | | | | 3 | 28.5 | 65.4 | 1.6 | 3.2/1.0/0.3 |
| | | | | | | 4 | 24.4 | 67.6 | 1.6 | 3.7/1.2/1.0 |
| 10 | 62/0.5 | 0.5 | 186/20 | 28/0.175 | 30 | 2 | 28.4 | 65.8 | 1.6 | 3.2/1.0/— |
| | | | | | | 3 | 25.8 | 67.5 | 1.6 | 36/1.1/0.3 |
| | | | | | | 4 | 26.0 | 67.8 | 1.7 | 3.4/1.1/— |
| 11 | 62/0.5 | 0.1 | 186/20 | 32/0.2 | 30 | 3 | 39.0 | 56.8 | 1.4 | 1.9/0.6/0.2 |
| | | | | | | 5 | 29.1 | 65.3 | 1.7 | 3.0/0.9/0.1 |
| 12 | 62/0.5 | 0 | 186/20 | 32/0.2 | 30 | 3 | 63.2 | 32.0 | 1.3 | — |
| | | | | | | 5 | 48.1 | 45.9 | 1.4 | 0.81/—/— |
| | | | | | | 7 | 31.6 | 62.2 | 1.9 | 1.8/0.9/— |
| 13 | 123/1.0 | 0.2 | 370/20 | 64/0.4 | 26–30 | 3 | 45.0 | 51.7 | 1.4 | 1.5/0.5/— |
| | | | | | | 6 | 33.9 | 60.0 | 1.5 | 2.4/0.7/— |
| | | | | | | o.n. | 25.0 | 68.7 | 0.9 | 3.6/1.1/0.3 |
| 14 | 62/0.5 | 0.5 | 186/15 | 32/0.2 | 15–25 | 2 | 56.4 | 40.0 | 1.0 | — |
| | | | | | | 4 | 45.9 | 50.8 | 1.1 | 1.1/0.3/0.1 |
| | | | | | | 6 | 36.6 | 57.5 | 1.2 | 1.9/0.4/0.8 |
| 15 | 62/0.5 | 0.5 | 186/20 | 32/0.2 | 15–27 | 2 | 55.1 | 36.4 | 1.3 | —/0.7/0.7 |
| | | | | | | 4 | 39.5 | 53.7 | 1.4 | 1.5/0.3/0.8 |
| | | | | | | 6 | 36.1 | 58.1 | 1.4 | 1.5/0.5/0.3 |
| 16 | 62/0.5 | 0.5 | 186/20 | 32/0.2 | 20–30 | 2 | 40.8 | 53.6 | 1.3 | 1.3/0.7/0.2 |
| | | | | | | 4 | 33.2 | 63.7 | 1.7 | 1.5/0.4/0.2 |

EXAMPLE 17

Preparation of MBA Using Prepared Solid Sodium Methoxide

A 1-l reactor, equipped with a mechanical stirrer and a reflux condenser, is charged with 60 ml toluene, BNB (60.6 g, 0.3 mol), sodium methoxide powder (19.4 g, 0.36 mol), solid KOH powder (33.6 g, 0.51 mol) and tetrabutylammonium bromide (18.2 g, 0.056 mol). The reaction is carried out with the forced passage of air through the reaction solution, in order to quench undesirable radical processes.

The heterogeneous mixture is stirred vigorously at 50° C. for 1–2 h (GC analysis shows >99% conversion of BNB). The mixture is then cooled and washed with water to remove inorganic compounds, followed by phase separation. The organic phase is washed with aq. HCl solution to remove PTC and the products of its decomposition remaining after the washing with water. Gas chromatography of the organic phase obtained after the separation shows the MBA content to be 97% (area %); less than 0.2% reduction products are formed.

Alternatively, instead of washing with water, all the inorganics may be filtered, followed by aq. HCl treatment of the organic phase. The organic phase is distilled to afford a final pure MBA (see Example 27).

EXAMPLE 18

The procedure described in Example 17 is followed, except that solid potassium methoxide is substituted for sodium methoxide. After 1 hour, the reaction mass is analyzed by gas chromatography. The analysis shows the MBA content to be 95% (area %).

EXAMPLE 19

The procedure described in Example 17 is followed, except that no potassium hydroxide is applied. After 4 hours, the reaction mixture is analyzed by gas chromatography. The analysis shows the MBA content to be 52% (GC area ). The reaction was allowed to proceed an additional 2 hours. However, according to gas chromatography, the content of MBA in the reaction mixture did not change.

It is clear that without potassium hydroxide, the reaction does not go to completion.

EXAMPLE 20

The procedure described in Example 17 is followed, except that the amount of potassium hydroxide applied is 1 mol per mol BNB. After 5 hours, the reaction mixture is analyzed by gas chromatography. The analysis shows the MBA content to be 85% (GC area). About 9% by-products, mainly reduction products, are formed. It is clear that the amount of KOH employed in this example is insufficient for the methoxydenitration to be satisfactorily selective.

EXAMPLE 21

The procedure described in Example 17 is followed, except that the amount of potassium hydroxide applied is 1.2 mol per mol BNB. After 1.5 hours, the reaction mixture is analyzed by gas chromatography. The analysis shows the MBA content to be 89% (GC area ). About 6% reduction products are formed.

EXAMPLE 22

The procedure described in Example 17 is followed, except that the amount of potassium hydroxide applied is 1.4 mol per mol BNB. After 2 hours, the reaction mixture is analyzed by gas chromatography. The analysis shows the MBA content to be 94% (GC area ). About 4% reduction products are formed.

EXAMPLE 23

The procedure described in Example 17 is followed, except that the amount of potassium hydroxide applied is 1.5 mol per mol BNB. After 2 hours, the reaction mixture is analyzed by gas chromatography. The analysis shows the MBA content to be 95% (GC area).

EXAMPLE 24

The procedure described in Example 17 is followed, except no phase transfer catalyst is used. After 3 hours, the gas chromatography analysis of the reaction mass shows no MBA. It is clear that without the phase transfer catalyst, the methoxydenitration does not proceed.

EXAMPLE 25

The procedure described in Example 17 is followed, except that the amount of tetrabutylammonium bromide is 15% w/w per initial BNB. After 5 hours, the reaction mass is analyzed by gas chromatography. The analysis shows the MBA content to be 84% (area %). About 14% by-products, largely reduction products, are formed.

It is clear that the amount of PTC employed in this example is insufficient for the methoxydenitration to be satisfactorily selective.

EXAMPLE 26

The procedure described in Example 17 is followed, except that the amount of tetrabutylammonium bromide is 20% w/w per initial BNB. After 2 hours, the reaction mass is analyzed by gas chromatography. The analysis shows the MBA content to be 92% (area %). About 6% reduction products are formed.

EXAMPLE 27

Preparation of MBA Using Potassium Methoxide Prepared In Situ.
Distillation of MBA A 1-l reactor, equipped with a mechanical stirrer and a reflux condenser is charged with toluene (175 g), methanol (38.4 g, 1.2 mol), solid KOH pellets (158.1 g, 2.4 mol) and tetrabutylammonium bromide (50.5 g, 0.157 mol). The heterogeneous mixture is stirred vigorously at 55–60° C. for about 15 minutes. Meanwhile, 3-bromonitrobenzene (202 g, 1 mol) and toluene (90 g) are heated to 50° C. in a separate vessel and the clear solution thus prepared is added dropwise over 0.5 hr. The reaction is carried out with the forced passage of air through the reaction solution in order to quench undesirable radical processes. The heterogeneous reaction mixture is stirred at 55–60° C. for 2 hr (GC analysis shows >99% conversion of BNB). The mixture is then cooled and washed with water to remove inorganic compounds, followed by phase separation. The organic phase is washed with aq. HCl solution to remove phase transfer catalyst and products of its decomposition remaining after the washing with water. Gas chromatography of the organic phase obtained after the separation shows the MBA content to be 97% (area %); less than 0.2% reduction products are formed.

After evaporation of the toluene under reduced pressure, the yellow-brown crude MBA was distilled fractionally under vacuum, by means of a distillation column with 5 theoretical stages equipped with a distillation head. The first fraction of the top temperature up to 123° C. (49 mm Hg) consists largely of the remaining toluene and a little MBA (1–2%, GC). The target fraction (155 g) of top temperature 123.3–124° C. was MBA of more than 99.5% purity according to gas chromatography. The principal impurities in the product are toluene and nitrobenzene. The yield of the pure MBA was 83% with respect to BNB.

Solid NaOH or KOH (~2% w/w per crude MBA) may be added to the distillation bottom to prevent coloration of the distilled MBA, which otherwise is obtained as a slightly yellow liquid.

EXAMPLES 28–31

The methods are the same as in Example 27, except that tetrabutylammonium chloride, tetrabutylammonium hydroxide, tetrabutylammonium hydrogen sulfate and tributylmethylammonium chloride are used as phase transfer catalysts in place of the tetrabutylammonium bromide. After 2 hours, the reaction mass is analyzed by gas chromatography. The analysis shows the MBA content to be 96–97% (area %) for each PTC.

EXAMPLE 32

The procedure described in Example 27 is followed, except that the amount of tetrabutylammonium bromide is 15% w/w per starting BNB. After 3.5 hours, the reaction mass is analyzed by gas chromatography. The analysis shows the MBA content to be 72% (area %). About 22% by-products, largely reduction products, are formed.

It is clear that the amount of PTC employed in this example is insufficient for the reaction to be satisfactorily selective.

EXAMPLE 33

The procedure described in Example 27 is followed, except that the amount of tetrabutylammonium bromide is 20% w/w per starting BNB. After 2 hours, the reaction mass is analyzed by gas chromatography. The analysis shows the MBA content to be 92% (area %). About 5% reduction products are formed.

EXAMPLE 34

The procedure described in Example 27 is followed, except that the amount of potassium hydroxide applied is 2 mol per mol BNB. After 2.5 hours, the reaction mass is analyzed by gas chromatography. The analysis shows the MBA content to be 91% (GC area). About 8% reduction products are formed.

EXAMPLE 35

The procedure described in Example 27 is followed, except that the amount of potassium hydroxide applied is 2.2 mol per mol BNB. After 2.5 hours, the reaction mass is analyzed by gas chromatography. The analysis shows the MBA content to be 95% (GC area).

EXAMPLE 36

The procedure described in Example 27 is followed, except that sodium hydroxide is substituted for the potassium hydroxide. After 6 hours, the reaction mass is analyzed by gas chromatography. The analysis shows the MBA content to be 71% (area %).

It is clear that sodium methoxide prepared in situ in the course of the reaction is significantly less reactive than potassium methoxide obtained in a similar way.

All the above descriptions and examples have been provided for the purpose of illustration, and are not intended to limit the invention in any way. Many modifications can be carried out in the process of the invention; for instance, various catalysts, solvents and reagents can be used, at different reaction conditions, all without exceeding the scope of the invention.

What is claimed is:

1. A process for the preparation of 3-bromoanisole comprising the steps of
   (a) Reacting nitrobenzene with bromine in oleum as the reaction medium to produce 3-bromo-nitrobenzene; and
   (b) methoxydenitration of the formed 3-bromonitrobenzene in the presence of a phase-transfer catalyst (PTC).

2. A process according to claim 1, wherein said methoxy-denitration is carried out utilizing a methoxydenitration reagent comprising an alkali metal methoxide.

3. A process according to claim 2, wherein said metal methoxide is selected from the group consisting of sodium methoxide and potassium methoxide.

4. A process according to claim 2, wherein said methoxy-denitration of 3-bromonitrobenzene is carried out in a water-immiscible nonpolar aprotic medium, and wherein said phase transfer catalyst comprises an effective amount of a quaternary ammonium salt.

5. A process according to claim 4, wherein said alkali metal methoxide comprises a pre-prepared solid alkali metal methoxide, and wherein said methoxydenitration is carried out in the presence of potassium hydroxide.

6. A process according to claim 5, wherein the amount of said alkali metal methoxide is 1.0–1.5 mol, based on 1 mol of bromonitrobenzene.

7. A process according to claim 4, wherein said alkali metal methoxide is selected from the group consisting of sodium methoxide and potassium methoxide.

8. A process according to claim 4, wherein said methoxy-denitration is carried out in the presence of potassium hydroxide, and wherein the molar ratio of said potassium hydroxide to said 3-bromonitrobenzene is 1.2–1.7.

9. A process according to claim 2, in which said alkali metal methoxide is prepared in situ by the reaction of the corresponding hydroxide and methanol.

10. A process according to claim 9, wherein said alkali metal methoxide comprises potassium methoxide and said corresponding hydroxide comprises potassium hydroxide.

11. A process according to claim 10, wherein the molar ratio of said methanol to said 3-bromonitrobenzene is 1.1–1.2.

12. A process according to claim 10, wherein the molar ratio of said potassium hydroxide to said 3-bromonitrobenzene is 2.2–2.4.

13. A process according to claim 5, wherein the reaction temperature is between about 40 to 80° C.

14. A process according to claim 9, wherein the reaction temperature is between about 50 to 80° C.

15. A process according to claim 1, wherein the concentration of said phase transfer catalyst is in the range of 20 to 30 wt % relative to said 3-bromonitrobenzene.

16. A process according to claim 1, wherein the phase transfer catalyst is selected from the group consisting of tributylmethylammonium chloride, tetrabutylammonium chloride, tetrabutylammonium hydroxide, tetrabutylammonium hydrogen sulfate, and tetrabutylammonium bromide.

17. A process according to claim 16, wherein the phase transfer catalyst is tetrabutylammonium bromide.

18. A process according to claim 1, wherein iodine is present in step (a) in an amount of up to 5% by weight relative to said nitrobenzene.

19. A process according to claim 18, wherein said nitrobenzene is brominated in oleum.

20. A process according to claim 18, wherein said oleum contains about 1–65% free $SO_3$.

21. A process according to claim 20, wherein the oleum contains about 15–30% free $SO_3$.

22. A process according to claim 19 carried out in the presence of iodine.

23. A process according to claim 22, wherein said iodine is present in an amount of 0–5% weight % relative to said nitrobenzene.

24. A process according to claim 23, wherein said iodine is present in an amount of 0.2–0.5 weight % relative to said nitrobenzene.

25. A process according to claim 18, wherein the reaction temperature is between about 0–100°.

26. A process according to claim 25, wherein the reaction temperature is between about 20–40° C.

27. A process according to claim 18, wherein the oleum/nitrobenzene weight ratio is between about 1.5 and 10.

28. A process according to claim 18, wherein the $Br_2$/nitrobenzene molar ratio is in the range of 0.3 to 1.0.

29. A process according to claim 28, wherein the $Br_2$/nitrobenzene molar ratio is in the range of 0.4 to 0.5.

30. A process according to claim 18, wherein said reacting of said nitrobenzene with said bromine further comprises the steps of:

a) diluting with water; and b) phase separation at a temperature above 50° C.

31. A process according to claim 18, wherein said reacting of said nitrobenzene with said bromine further comprises the steps of:

a) diluting with water; and b) cooling and filtering the crystallized 3-bromonitrobenzene.

32. A process according to claim 18, wherein said reacting of said nitrobenzene with said bromine further comprises the steps of:

a) diluting with water; and b) extracting the 3-bromonitrobenzene with an organic solvent; and c) phase separation.

33. A process according to claim 32, wherein the organic solvent is selected from the group consisting of from dichloroethane, dichloromethane, toluene, xylene and cyclohexane.

34. A process according to claim 4, wherein said medium is selected from the group consisting of cyclohexane, hexane, heptane, octane, nonane, toluene and xylenes.

35. A process according to claim 34, wherein said medium comprises toluene.

* * * * *

UNITED STATES PATENT AND TRADEMARK OFFICE
CERTIFICATE OF CORRECTION

PATENT NO.   : 6,380,440 B1
DATED        : April 30, 2002
INVENTOR(S)  : Mark Gelmont and Joseph Zilberman It is certified that error appears in the above-identified patent and that said Letters Patent is hereby corrected as shown below:

<u>Title page,</u>
Delete the ABSTRACT and insert the following ABSTRACT:
-- Processes are disclosed for the preparation of 3-bromoanisole including reacting nitrobenzene with bromine in oleum to produce 3-bromonitrobenzene and methoxydenitration of the 3-bromonitrobenzene in the presence of a phase-transfer catalyst. --

<u>Column 1,</u>
Line 32, "It is" should begin a new paragraph.
Line 54, delete comma following "use".

<u>Column 2,</u>
Line 40, "rang" should read -- range --.
Line 41, before "0-5%" insert -- of --.

<u>Column 4,</u>
Line 66, "Brorination" should read -- Bromination --.

<u>Column 8,</u>
Line 59, "wlw" should read -- w/w --.

<u>Column 12,</u>
Line 9, delete "from".

Signed and Sealed this

Twenty-ninth Day of October, 2002

*Attest:*

*Attesting Officer*

JAMES E. ROGAN
*Director of the United States Patent and Trademark Office*